United States Patent [19]
Shepard

[11] 3,983,865
[45] Oct. 5, 1976

[54] METHOD AND APPARATUS FOR MYOFUNCTIONAL BIOFEEDBACK
[76] Inventor: Richard S. Shepard, 1222 El Nido Drive, Fallbrook, Calif. 92028
[22] Filed: Feb. 5, 1975
[21] Appl. No.: 547,235

[52] U.S. Cl. ............................. 128/2.1 M; 128/2 S
[51] Int. Cl.² .......................................... A61B 5/05
[58] Field of Search .......... 128/2.1 R, 2.1 M, 2.1 E, 128/2.1 B, 2.1 Z, 2 N, 2 S

[56] References Cited
UNITED STATES PATENTS

| | | | |
|---|---|---|---|
| 3,131,689 | 5/1964 | Rodler | 128/2.1 Z |
| 3,628,538 | 12/1971 | Vincent et al. | 128/2.1 M |
| 3,641,993 | 2/1972 | Gaarder | 128/2.1 M |
| 3,662,746 | 5/1972 | Saltzberg et al. | 128/2.1 M |
| 3,802,419 | 4/1974 | Yates | 128/2.1 R |

Primary Examiner—Robert W. Michell
Assistant Examiner—Lee S. Cohen
Attorney, Agent, or Firm—Fulwider, Patton, Rieber, Lee & Utecht

[57] ABSTRACT

A method and apparatus for performing myofunctional therapy by way of biofeedback comprising a plurality of electrodes disposed along a patient's upper jaw, each connected to a detector circuit. An externally applied low voltage signal is selectively passed to respective ones of the detector circuits when the corresponding electrode is contacted by the tongue, whereby the detector circuit illuminates an associated light-emitting diode indicating such contact. In addition, a differential mode discriminating circuit is connected to selected facial muscles to register the electrical activity therein, again providing illuminated display if the muscular electrical levels are above a selected threshold.

11 Claims, 2 Drawing Figures

METHOD AND APPARATUS FOR MYOFUNCTIONAL BIOFEEDBACK

BACKGROUND OF THE INVENTION

1. Field of the Invention

The present invention relates to myofunctional therapy biofeedback devices, and more particularly to a biofeedback device adapted to sense the motion sequence of a tongue during swallowing and speech in coherent relationship with the tensioning of selected facial muscles.

2. Description of the Prior Art

In the field of myofunctional therapy, efforts generally expended in aligning the bite are often undone by abnormal swallowing and speech habits developed prior to the corrective work. In the past, various techniques have been developed by which the proper alignment of musculature at any one discrete point during the swallowing cycle is measured; however, none of those techniques monitor the whole sequence of significant muscular movements during the swallow. Most prior art devices of this kind do not provide a ready visual display to the patient by which the patient himself could notice, without the aid of other persons in attendance, the immediate propriety of his muscular position. Lacking such readily obtainable indication, any corrective therapy would necessarily require the attendance of other persons, thus raising the expense and the frequency of therapeutic exercises. Furthermore, most prior art devices only measure a singular position of the tongue and therefore provide no information to either the patient or the therapist as to the propriety of the sequence of muscular movements that has occurred. Often the sequence entails small, and therefore visually hard to perceive, concurrent muscular contractions such as contractions of the facial muscles which occur both during a swallow and during speech and which therefore call for extensive visual inspection by a trained person in order to arrive at a proper diagnosis.

Accordingly, there is a present need for an appliance which by virtue of its simplicity could be conveniently bought, leased out by the patient, or used by a therapist during the therapy periods, such appliance having the requisite qualities of simplicity of operation and an easily comprehended display. Since the swallowing sequence often involves muscular contractions which are essentially on the subconscious level, or the motor level, the display therefore would be providing biofeedback. In addition, a device of such kind would necessarily also involve convenient adjustment features by which the therapist could progressively trim up the training program until proper speech or swallow habits are obtained. Further, the same device could be utilized for diagnostic readings by adjusting the various components thereof to known normals.

SUMMARY OF THE INVENTION

It is therefore the general purpose and object of the present invention to provide a diagnostic device adapted to monitor the muscular contraction sequence occurring during swallowing and speech. Further objects of the invention are to provide, by way of the same diagnostic device, a convenient display set by the therapist by which selected therapeutic exercises could be carried out. Yet further objects of the present invention are to provide a diagnostic device which could be set for various other abnormal muscular sequences, including abnormal joint problems, and which could subsequently be gradually corrected to a proper sequence.

Briefly, these and other objects are accomplished within the present invention by providing a plurality of electrodes mounted in a fixture aligning such electrodes behind the front teeth and in selected positions along the roof of the mouth, to be contacted in sequence by the tongue both during speech and swallowing. In order to provide an electrical signal through such electrodes when touched by the tongue, an externally applied signal source electrode is also provided, attachable to any surface of the body, the signal source electrode connecting to an oscillator circuit. The body of the patient is therefore excited by the oscillator circuit by a selected frequency electrical signal, at signal levels below any level potentially hazardous to the patient. The tongue, during passing, therefore completes the circuit across the electrodes within the mouth and the oscillatory signal is brought out to the exterior of the mouth on insulated leads. Thus each electrode is brought out by way of an insulated lead to a corresponding filter amplifier set at a bandpass centered about the externally imposed oscillation frequency. The outputs of the respective filter amplifiers are then rectified in corresponding A.C.-to-D.C. converters, where each converter output is, in turn, connected to an associated adjustable voltage comparator. The respective outputs of the comparators are then connected to corresponding indicator lights to provide a visual display.

In addition to the above-mentioned electrodes, there is a set of externally applicable sensors mounted on an externally attachable elastic base, the sensors connecting to operational amplifiers arranged in a differential mode. The operational amplifiers form bandpass filters passing the frequency band associated with the biological discharge frequency domain which occurs in the process of the contraction of a muscle. By way of this lately referred to set of sensors, a measurement is also taken of any selected facial muscle which when converted to a D.C. signal is displayed on a meter and compared to a reference voltage which, when exceeded, illuminates additional light-emitting diodes.

DESCRIPTION OF THE SPECIFIC EMBODIMENT

Figures 1, 2:
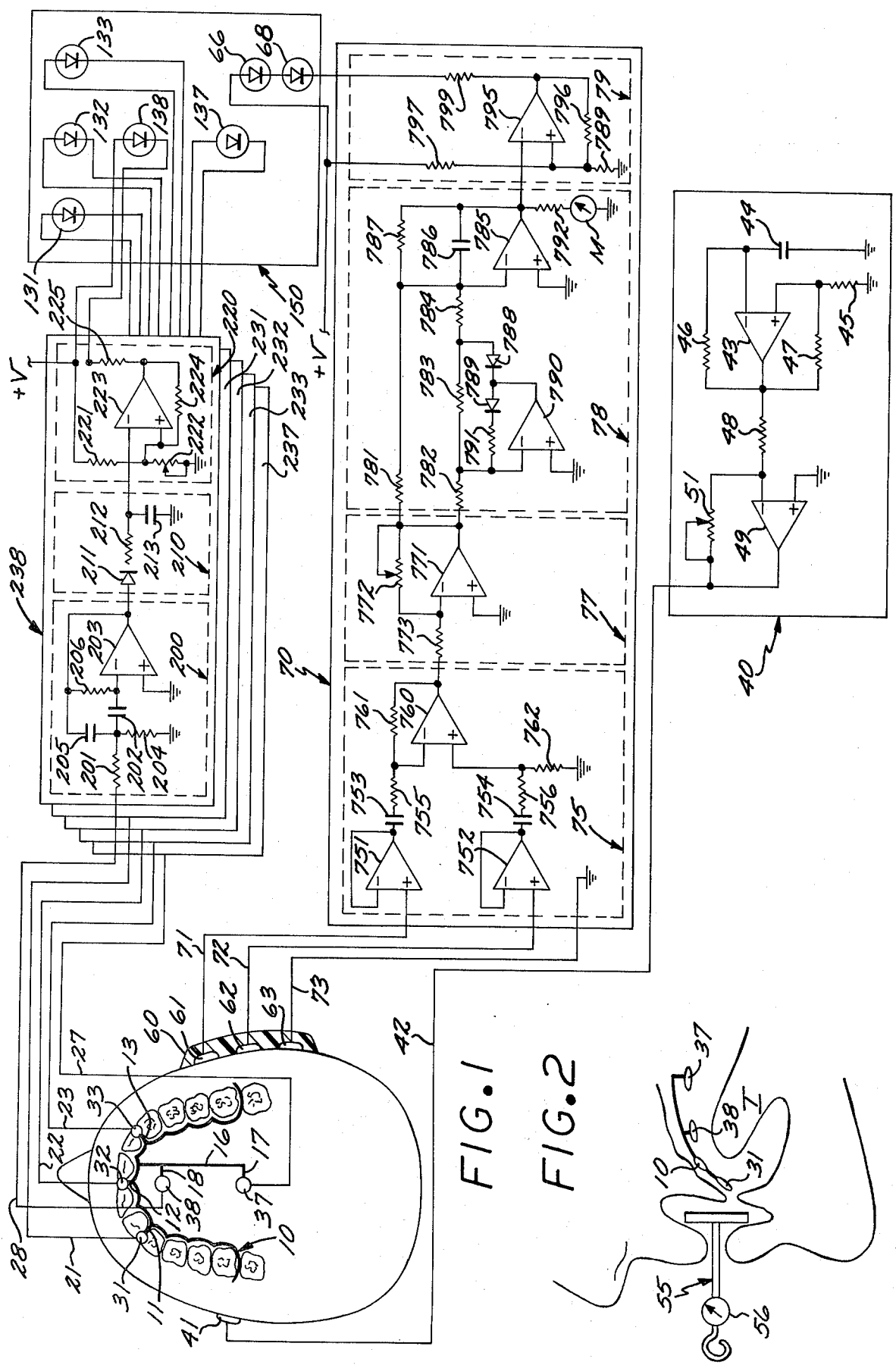
FIG. 1 is a diagrammatic illustration of the inventive device arranged to sense and display the tongue and muscular movements of a patient.
FIG. 2 is a side view, in partial cross section, of a patient's mouth illustrating a position of the patient's tongue relative the electrodes of the device shown in FIG. 1.

While the present invention is described with reference to a swallow, speech and tempro-mandibular joint diagnostic and therapy device, such reference is for purposes of clarity only. Although particularly adapted for such use, other uses are envisioned therefor, and no intent to limit the scope of the invention is expressed hereby.

As shown in FIG. 1, a holding fixture, generally designated by the numeral 10, is formed in the manner of a bent wire convolved on the interior surfaces of the teeth of a patient. The general shape of the wire holding fixture 10 is that of a horseshoe, aligning within the curvature of the upper jaw. Extending peripherally and radially along the inner surface of the teeth to the exterior of the central segment of fixture 10 are a plurality of mounts 11, 12 and 13, mount 12 being disposed substantially central to the jaw while mounts 11 and 13 being disposed laterally on either side thereof. Extending in an opposed direction to mount 12, along the roof of the mouth, is a support member 16 terminating in an end mount 17 and an intermediate mount 18 aligned with the incisive papillae of the mouth. Mounts 11, 12, 13, 17 and 18 are also formed in the manner of a bent wire, each retaining on the ends thereof a corresponding electrode, respectively designated electrodes 31, 32, 33, 37 and 38. Electrodes 31, 32, 33, 37 and 38 connect to corresponding leads 21, 22, 23, 27 and 28. It is to be understood that the last digit within the designating numerals for the respective mounts, insulated leads and corresponding electrodes indicate a collected relationship whereby, for example, mount 11 clasps the insulated lead 21, lead 21 terminating in the exposed electrode 31. For the intended use, it is further contemplated that the support member 16 and the fixture 10 both comprise an easily deformable wire structure adapted to conform to the dimensions of the roof of the mouth and the teeth surfaces. Furthermore, mounts 11, 12, 13, 17 and 18 similarly comprise segments of wire of like deformability thus allowing for manipulation and selective alignment of the electrodes. In this manner, selective disposition of the electrodes within the mouth of the patient can be made by the therapist for selective contact with the tongue.

As shown in FIG. 2, the initial proper position of the tongue, designated T, is against the incisive papillae so that when proper initial tongue alignment is made, tongue T contacts electrode 38. As the swallow progresses, electrode 37 is sequentially contacted. Electrodes 31, 32 and 33, on the other hand, provide only an improper indication of initial tongue portion, and should such occur during any portion of the swallow sequence, it is intended that the signals from such indicate an improper reading.

Referring back to FIG. 1, an external signal source electrode 41 is shown applied to the exterior face surface, electrode 41 terminating in a lead 42 which connects to an oscillator circuit 40.

In addition to the above electrodes, an externally applicable elastomer sensor fixture, or pad, 60 is illustrated on the side of the patient's face in FIG. 1. The sensor pad 60 includes sensors 61, 62 and 63 buried within the interior thereof, sensors 61, 62 and 63 being aligned to contact the skin of the patient. Accordingly, any galvanic activity occurring in the underlying muscle is sensed across sensors 61 and 62, sensor 63 providing the ground reference.

Sensors 61, 62 and 63 are connected by corresponding leads 71, 72 and 73 to a measurement circuit 70, leads 71 and 72 connecting to the input of a differentially connected amplifier stage 75 and lead 73 being tied to the circuit ground. Within stage 75 lead 71 connects to the noninverting terminal of an operational amplifier 751 which at its negative terminal includes a unit gain feedback connection to the output. Similarly, lead 72 connects to an operational amplifier 752 on the input side of stage 75, amplifier 752 again including a unity gain feedback connection. The outputs of amplifiers 751 and 752 are connected respectively across a coupling capacitor 753 in series with an input resistor 755 and a capacitor 754 in series with a resistor 756, to the inverting and noninverting inputs of an operational amplifier 760.

Operational amplifier 760 includes a negative feedback connection formed by a resistor 761 and is tied to ground at the noninverting input across a resistor 762. Amplifiers 751, 752 and 760 thus form a circuit connected in differential mode, providing both high input impedance relative skin impedance variations, good rejection of the common mode and a single ended output.

The output of amplifier 760 connects to a variable gain stage 77. Stage 77 includes an operational amplifier 771 adjustable in gain by way of a variable feedback resistor 772. Amplifier 771 receives, at the inverting terminal, the output of amplifier 760 across an input resistor 773. Stage 77 thus provides for convenient gain setting such that physiological signals at various levels can be sensed.

The output of amplifier 771 is converted to a D.C. signal in an A.C.-to-D.C. converter circuit 78. More specifically, the output of amplifier 771 is connected to a resistor 781 connected in parallel across a series circuit comprising resistors 782, 783 and 784. The other end of resistor 781 connects to the inverting input of yet another operational amplifier 785 configured as a low pass filter by way of a feedback capacitor 786 and feedback resistor 787.

Connected across resistor 783 is a rectifying circuit comprising a diode 788 in series with a diode 789 and a resistor 791. Diode 789 and resistor 791 in turn form an output-to-input return around an operational amplifier 790. Thus, the signal out of amplifier 771 is rectified by the circuit around amplfier 790 and is then smoothed across amplifier 785. Amplifier 785 then connects both to a meter M, across a resistor 792, and a compartor circuit 79. Comparator circuit 79 comprises a voltage comparator formed around an operational amplifier 795 including a positive feedback resistor 796. The noninverting terminal of amplifier 795 furthermore connects to the division point of a divider comprising resistors 797 and 789 between a signal source +V and ground, which sets the comparison voltage. The output of amplifier 795 then connects, across a resistor 799, to two series connected light-emitting diodes 66 and 68 mounted on a display board 150. Diodes 66 and 68 complete a circuit between the signal source +V and the output of comparator 79 and will light up each time amplifier 795 swings low.

The display board 150 also includes light-emitting diodes 131, 132, 133, 137 and 138 arranged in a geometric correspondence with the arrangement of electrodes 31, 32, 33, 37 and 38 within the mouth of the patient. Diodes 131, 132, 133, 137 and 138 therefore provide a visual indication of the contacts made by the tongue T, or of the tongue position, as detected by a set of corresponding detector circuits 231, 232, 233, 237 and 238.

Since each detector circuit functions, and is therefore constructed, in an identical manner, only one such circuit, 238, is described in detail herein, it being understood that circuits 231, 232, 233 and 237 are identical copies thereof.

Detector circuit 238 connects at the input to lead 28 which communicates to the interior thereof to form the input to a filter amplifier stage 200. Within stage 200, lead 28 is connected across an input resistor 201 in series with a coupling capacitor 202 to the inverting terminal of an operational amplifier 203. The juncture between resistor 201 and capacitor 202 is both tied to ground across a resistor 204 and to the output of amplifier 203 across a feedback capacitor 205. In addition to the capacitive feedback, a feedback resistor 206 is provided between the inverting input terminal and output of amplifier 203.

Stage 200 therefore is configured as a bandpass filter set to pass the frequency generated by the oscillator circuit 40 by conventional selection of the capacitive and resistive components therein. The passed oscillatory output signal thereof is converted to a D.C. signal by an A.C.-to-D.C. converter stage 210. Stage 210 includes a series circuit comprising a diode 211 and a resistor 212, smoothed by a capacitor 213 to ground, rectifying and connecting the output of amplifier 203 to the input of a comparator stage 220. Stage 220 is similar in configuration to stage 79 described above, including a divider network comprising an upper resistor 221 and a lower variable resistor 222 tied between the signal source +V and ground. This divider sets the reference voltage at the noniverting terminal of an operational amplifier 223 which, similar to amplifier 795, includes a positive feedback resistor 224 and receives the rectified signal at the inverting terminal. The output of amplifier 223 then ties across a resistor 225 to the cathode of the diode 138, on the display board 150, which at the anode is again tied to the signal source +V.

Diodes 131, 132, 133 and 137 are similarly connected to the corresponding detector circuits 231, 232, 233 and 237. Thus each time a tongue contact is made with any of the electrodes, a corresponding displayed diode lights up. By proper tutoring, the patient is trained to light up only certain diodes, thus allowing for corrective therapeutic exercises to correct abnormal conditions.

In order to provide excitation to the detector circuits, the aforementioned oscillator circuit 40 is connected to the body of the patient. While there are various ways of providing an oscillating signal, one example of such is included herein by way of the structure of circuit 40. More specifically, circuit 40 includes a first operational amplifier 43 tied to ground at the inverting terminal across a capacitor 44. The noninverting terminal of amplifier 43 is in turn tied to ground across a resistor 45. The inverting and non-inverting terminal furthermore connect to the amplifier output across respective negative and positive feedback resistors 46 and 47.

The output of amplifier 43 then connects across an input resistor 48 to the inverting terminal of yet another amplifier 49 which includes a variable resistor 51 forming a negative feedback thereacross. The output of amplifier 49 then connects to the lead 42 which at the other end superposes an oscillatory, low current, low voltage signal to the patient's body.

The method of correlating the above-described apparatus is now set forth with particular reference to FIG. 2. As shown in FIG. 2, the measurement of facial muscles can be controlled by way of a conventional 2.5 cm calibration instrument 55 which is provided with a load measuring indicator 56. One end of the instrument 55 is retained by the patient's embouchure and the withdrawal force is thus measured concurrently with the reading of meter M. The gain of stage 77 is then adjusted at the supplier's facility to light up diodes 66 and 68 upon achievement of proper muscular tension levels. Once set, the meter M can be used to measure the muscular levels of any patient. Diodes 131, 132, 133, 137 and 138 provide the tongue position indication. Upon reaching a proper lighting combination of the diodes, the patient can then proceed with repetitive exercises until proper habits are achieved.

The many advantages of the present invention should now be readily apparent. The invention provides a convenient device by which various tongue positions can be monitored and which renders unattended thereapeutic exercises feasible. Such features are carried out by apparatus which is simple to produce, requires few adjustments and is conveniently adaptable to various patients.

Obviously, many modifications and variations of the present invention may be made with regard to the foregoing detailed description without departing from the spirit of the invention.

I claim:

1. Apparatus for monitoring physiological movements of a patient, comprising:
   a plurality of first electrodes adapted to be contacted by selected parts of the body of the patient during movement thereof;
   means for providing an oscillatory source of electrical excitation externally applied to the body of the patient for conduction through said first electrodes when said first electrodes are contacted;
   a plurality of detecting means, each respectively connected to corresponding ones of said first electrodes for producing first binary signals indicative of contacts made with said corresponding first electrodes in response to the conduction of said oscillatory signal thereacross;
   signal discriminating means including a plurality of second electrode at the input thereof adapted to be connected to selected skin areas of said patient overlying selected muscles cooperating with said selected parts of the body, said discriminating means producing a second binary signal indicative of the subject physiological electrical levels thereat; and
   display means for receiving said first and second binary signals for providing concurrent selected indications of the corresonding levels thereof.

2. Apparatus according to claim 1 further comprising:
   a wire fixture adapted to be conformed to selected interior surfaces of the patient's mouth including supports connected to said first electrodes aligned to be in selected opposition to the positions of the patient's tongue.

3. Apparatus according to claim 2 wherein:
   said detecting means each include a filter amplifier at the input thereof set to pass and said oscillatory signal; and
   said discriminating means includes a differentially connected amplifier at the input thereof for discriminating said physilogical electrical signals.

4. Apparatus according to claim 3 wherein:
   said display means includes a plurality of light-emitting diodes each connected to corresponding ones of said detecting and discriminating means to be illuminated by said first and second binary signals.

5. Apparatus according to claim 4 wherein:
   said detecting means each includes a first rectifying means connected to receive the output of said filter amplifier, and a first comparator connector connected to said rectifying means for producing said first binary signal according to the relative amplitude thereof; and said discriminating means includes an adjustable amplifier in circuit with said differentially connected amplifier, second rectifying means connected to the output of said adjustable amplifier, a meter connected to said second rectifying means for displaying the signal amplitude at the output thereof and a second comparator connected to said second rectifying means for producing said second binary signal according to the relative amplitude at the output thereof.

6. Apparatus for monitoring selected movements of a patient, comprising:

a plurality of electrodes adapted to be contacted by selected parts of the body of the patient during movement thereof;

means for providing an oscillatory electrical excitation externally applied to the body of the patient for conduction through said electrodes when said electrodes are contacted;

a plurality of detecting means each respectively connected to corresponding ones of said electrodes for producing binary signals indicative of contacts made with said corresponding electrodes in response to the conduction of said oscillatory signal thereacross each of said detecting means including a high impedance input connection relative to the contact impedance variations of its corresponding electrode; and display means for receiving said binary signals for providing concurrent selected indications of the corresponding levels thereof.

7. Apparatus according to claim 6 further comprising:

a wire fixture adapted to be conformed to selected interior surfaces of the patient's mouth including supports secured to said electrodes for disposing said elelctrodes in selected opposition to the positions of the patient's tongue.

8. Apparatus according to claim 7 wherein:

said detecting means each include a filter amplifier at the input thereof set to pass said oscillatory signal.

9. Apparatus according to claim 8 wherein:

said display means includes a plurality of light-emitting diodes each connected to corresponding ones of said detecting means to be illuminated in response to said binary signals.

10. A method for monitoring and displaying the positions of a patient's tongue in coordination with selected other facial muscles, comprising the steps of:

imposing an oscillatory electrical signal to the body of the patient;

aligning selected electrodes within the mouth of the patient for selective contact by the patient's tongue;

illuminating selected first light fixtures on a display by said oscillatory signal in association with said selective contacts;

measuring concurrently the physiological electrical signals in selected other facial muscles; and illuminating selected second light fixtures on a display in association with the magnitude of said physiological electrical signals.

11. A method according to claim 10 comprising the further steps of:

correlating the physiological electrical signals against a measured force; and adjusting the gain of the measurement according to such calibration.

* * * * *

UNITED STATES PATENT OFFICE
CERTIFICATE OF CORRECTION

Patent No. 3,983,865  Dated October 5, 1976

Inventor(s) Richard S. Shepard

It is certified that error appears in the above-identified patent and that said Letters Patent are hereby corrected as shown below:

Column 2, line 41, correct "lately" to read -- lastly --.
Claim 1, line 41, change "subject" to read -- subjacent --; Claim 3, line 54, delete "and"; Claim 5, line 67, delete "connector".

Signed and Sealed this

Fourth Day of January 1977

[SEAL]

Attest:

RUTH C. MASON
Attesting Officer

C. MARSHALL DANN
Commissioner of Patents and Trademarks